US006488690B1

(12) United States Patent
Morris et al.

(10) Patent No.: US 6,488,690 B1
(45) Date of Patent: Dec. 3, 2002

(54) SUTURE KNOT SEALING INSTRUMENTS AND METHODS OF USING THE SAME

(75) Inventors: John K. Morris, 3125 Hunting Valley, Ann Arbor, MI (US); Harry E. Colestock, Ann Arbor, MI (US)

(73) Assignee: John K. Morris, Ann Arbor, MI (US)

( * ) Notice: Subject to any disclaimer, the term of this patent is extended or adjusted under 35 U.S.C. 154(b) by 0 days.

(21) Appl. No.: 09/531,258

(22) Filed: Mar. 17, 2000

Related U.S. Application Data

(60) Provisional application No. 60/124,770, filed on Mar. 17, 1999.

(51) Int. Cl.[7] ............................. A61B 17/04; B25F 3/00
(52) U.S. Cl. ......................... 606/144; 30/124; 30/140; 289/17
(58) Field of Search ....................... 30/124, 140; 289/2, 289/17; 606/144, 145

(56) References Cited

U.S. PATENT DOCUMENTS

| | | | | |
|---|---|---|---|---|
| 3,354,478 A | * | 11/1967 | Allen ............................. | 30/140 |
| 4,516,574 A | * | 5/1985 | Hewes ........................... | 606/29 |
| 4,662,068 A | * | 5/1987 | Polonsky ....................... | 30/124 |
| 4,845,851 A | * | 7/1989 | Warthen ........................ | 30/140 |
| 5,087,263 A | * | 2/1992 | Li ................................. | 606/144 |
| 5,290,284 A | | 3/1994 | Adair ............................ | 606/37 |
| 5,292,327 A | * | 3/1994 | Dodd et al. ...................... | 606/1 |
| 5,306,280 A | | 4/1994 | Bregen et al. ................ | 606/143 |
| 5,403,330 A | * | 4/1995 | Tauson ........................ | 606/139 |
| 5,417,700 A | | 5/1995 | Egan ........................... | 606/144 |
| 5,423,837 A | * | 6/1995 | Mericle et al. .............. | 606/148 |
| 5,565,122 A | | 10/1996 | Zinnbauer et al. ........... | 219/227 |

OTHER PUBLICATIONS

Herrmann, J.B. "Tensile Strength and Knot Security of Surgical Suture Materials." *The American Surgeon*, Apr., 1971, pp. 209–217.

Tera, H. and Aberg, C. "Tensile Strenghts of Twelve Types of Knot Employed in Surgery, Using Different Suture Materials." Acta Chir Scand 142: 1–7, 1976.

(List continued on next page.)

*Primary Examiner*—Gary Jackson
(74) *Attorney, Agent, or Firm*—Gifford, Krass, Groh, Sprinkle, Anderson & Citkowski, PC

(57) ABSTRACT

A hand-held instrument coagulates suture knots for enhanced security, preferably applying heat to thermoplastic materials. The instrument includes a proximal end adapted for gripping by a user, and a distal tip with a heating element activated by a user control. A knot-retaining feature is provided which allows the tool to function as a knot slider or pusher prior to sealing. The retaining feature may be a fork-shaped element, or may including a surface in communication with a tube, channel or groove, tube, enabling one or more strands of suture material to be dressed away from the tip when heated. The electrical conductors used to activate the heating element at the tip of the tool may be bipolar or unipolar, in which case the body of the patient is utilized as the return electrical path through a grounding pad. The tool may be entirely self-contained and battery operated, and the distal portion of the tool may be provided as a removable insert to existing Bovie instruments.

15 Claims, 1 Drawing Sheet

OTHER PUBLICATIONS

Burkhardt, S., Wirth, M., Simonick, M. Salen, D., Lanctot, D., and Athanasiou, K. "Loop Security as a Determinant of Tissue Fixation Security." Technical Note in Arthroscopy: The Journal of Arthroscopic and Related Surgery, vol. 14, No. 7 (Oct.), 1998: pp 773–776.

Loutzenheiser, T., Harryman, D., Yung, S., France, M. and Sidles, J. "Optimizing Arthroscopic Knots." in Arthroscopy: The Journal of Arthreoscopic and Related Surgery, vol. 11, No. 2 (Apr.), 1995: pp 199–206.

Holmlund, D. "Knot Properties Of Surgical Suture Materials." A Model Study in Acta Chir Acand 140: 355–362, 1974, pp 355–362.

Gartsman, G. and Hammerman, S. "Arthroscopic Repair of Full–THickness Rotator Cuff Tears: Operative Technique." Operative Techniques in Orthopaedics, vol. 8, No. 4 (Oct.), 1998: pp 226–235.

* cited by examiner

SUTURE KNOT SEALING INSTRUMENTS AND METHODS OF USING THE SAME

REFERENCE TO RELATED APPLICATION

This application claims priority of U.S. provisional patent application Serial No. 60/124,770, filed Mar. 17, 1999, the entire contents of which are incorporated herein by reference.

FIELD OF THE INVENTION

This invention relates generally to surgical suturing and, in particular, to instrumentation, and methods of using the same, for heat-sealing suture knots.

BACKGROUND OF THE INVENTION

Wound suturing and vessel ligation are still carried out largely done by hand. A thread attached to a curved needle is guided with forceps from one side of a wound to another, or around a vessel to be occluded. The thread is drawn tight, knotted and cut, and the process is repeated to form multiple stitches. Although the traditional approach is easily accomplished on external wounds, the process is more difficult when applied to internal body cavities, particularly when small incisions are used.

Manually tied sutures present certain problems. For one, surgical knots tied with smooth, thermoplastic materials such as nylon require great care to ensure that the knot does not loosen after closing. For this reason, various tools and techniques have been proposed to enhance knot security, including alternative knot styles and devices that use ultrasonic or thermal energy to join suture material without knots.

One such device is disclosed in U.S. Pat. No. 5,417,700, entitled AUTOMATIC SUTURING AND LIGATING DEVICE. According to this patent, a needle is used to form a passage through tissue, or around a vessel or duct. Suture material is threaded through the passage and secured, whereupon the needle is removed, leaving the thread. In a preferred embodiment, the device comprises two curved, opposed pincer-like needles which penetrate the tissue on either side of the wound, or surround the vessel or duct, with the needles meeting opposite the device. The thread is drawn and secured at a given tension, cut and the ends, and ultrasonically welded, afterwhich the device is removed, leaving a knot-free stitch or ligature.

U.S. Pat. No. 5,565,122 discloses a suture cutter including a housing with an electrical power source and a trigger having open and closed positions. A suture clamp with a stationary jaw and a pivoting jaw and radiant heating element is attached to the distal tip of the device. An actuator connects the trigger to the pivotal jaw and electrical circuitry, such that closing of the trigger holds a strand of suture material between the jaws, after which the strand is severed and cauterized using the radiant heating element.

Although devices of the type just described would appear to successfully cut and weld or coagulate individual suture fibers, they do not consider joining or sealing a partial or completed suture knot. In a growing number of surgical procedures, however, the need to fortify the suture knot itself is becoming more desirable if not necessary. Due to the increase in arthroscopic and laproscopic procedures to reduce incision magnitude and post-operative convalescence, an increasing number of knots must be tied within body cavities and through small openings. This may be technically cumbersome, time consuming, and occasionally ineffective compared to standard open techniques. Ironically, the low coefficient of friction that allows for sliding knots into a body cavity is the bane of knot or loop security.

According to journal articles directed to knot security, a serious pitfall in tying sutures is the formation of a sliding knot. In one experiment, the strength of a chromatic catgut loop fell from 3.23 kp to 0.15 kp when a sliding knot was used. Mersilene, Dexon, polyester, polyethylene, monofil nylon and silk all have significant failures (25 percent of the time) due to knot slippage, even with square knots.

Generally, the more knots that are tied, the more security is obtained. However, it has been reported that in the case of some common suture materials, an absolutely secure knot could not be obtained even with as many as six or seven well snugged-down throws. Teflon and silicone-impregnated sutures in particular exhibit this phenomenon. Indeed, a linear relationship appears to exist between the coefficient of friction with respect to a given suture material and relative knot security. Evidently, the low coefficient of friction that makes it easy to slide knots for arthroscopic-type procedures is also the reason behind low knot security using existing techniques.

SUMMARY OF THE INVENTION

The present invention solves problems associated with suture knot security by providing an instrument operative to coagulate and heat-seal suture knots incorporating thermoplastic materials. The instrument takes the form of an elongated tool having a proximal end adapted to gripping by a user, and a distal tip operative to at least partially melt a suture knot. It has been discovered that by heat-sealing the ends of various suture materials, the integrity of the given construct is dramatically increased, often doubling the holding power, thereby increasing the likelihood of a successful surgery.

In the preferred embodiment, a short channel is formed providing a path to the knot-melting region, allowing the tool to function as a knot slider or pusher prior to sealing. The channel may be in the form of a groove, tube or other feature enabling one or more strands of suture material to be dressed away from the tip when heated.

The electrical conductors used to activate the heating element at the tip of the tool may be bipolar or unipolar, in which case the body of the patient is used as the electrical return path. The tool may be entirely self-contained and battery operated, though, in the preferred embodiment, the distal portion of the tool is provided as a removable insert to existing Bovie instruments.

DETAILED DESCRIPTION OF THE INVENTION

Figure 1:
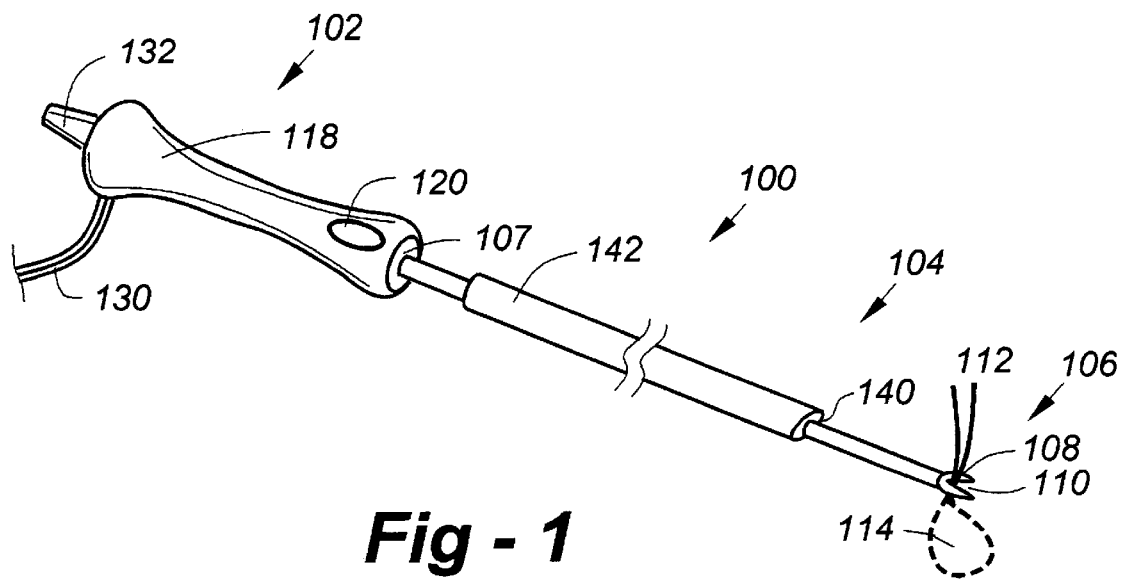
FIG. 1 is a drawing, seen from an oblique perspective, of an instrument according to the invention that may be used for open or arthroscopic surgical procedures.

FIG. 1 is a drawing of a device according to the invention, depicted generally at 100. Overall, the device takes the form of a hand-held instrument 100 having a proximal end 102 adapted for gripping by a user, and a distal end 104 having a distal tip 106. The distance between the handle and distal tip may be made relatively short for open cases, or more elongate for arthroscopic usage. An coupling may be provided, at point 107, for example, to accommodate multiple end portions of varying length to be interchanged for different applications.

In all embodiments, the distal tip of each instrument according to the invention includes a suture-knot retaining feature and means for coagulating the knot when so retained. In the preferred embodiment, a heating element is used to coagulate the retained knot, though the device may be modified to make alternative use of ultrasonic energy. The device may also use bipolar or unipolar electrical interconnections to the knot coagulation means. That is, both the power-supply and return-path wires may be brought to the coagulation element while being insulated from the body of the patient, or the patient's body may be used as the return path, as is typically the case with monopolar arrangements.

The embodiment depicted in FIG. 1 is a bipolar configuration, though it may be adapted for monopolar operation. Power is preferably supplied through batteries (not shown) disposed in the handle 118 of the device, or, optionally through wires 130 to an external power source (also not shown). A momentary contact pushbutton 120 is preferably provided at the proximal end 102 on handle 118 to selectively route power from the internal or external power source through a pair of insulated wires to the distal tip 106, with a manual control 132 such as a variable resistor being used to adjust power level and temperature in the case of a heating element.

In the embodiment of FIG. 1, the heating element 108 is formed into a fork-shaped knot retaining feature, enabling a slider-type knot 110 to be pushed down onto one of a pair of suture materials 112 to tighten a loop 114. Having done this, the control 120 is activated to simultaneously seal the knot 110 while cutting the sutures 112. Any suitable material may be used to form the heating element 108, though nichrome wire is preferably used in this embodiment. In the event that the knot is coagulated and sealed but the strands 112 not severed, a cutter may be provided, for example, in the form of a blade 140 attached to a moveable sleeve 142.

Figure 2:
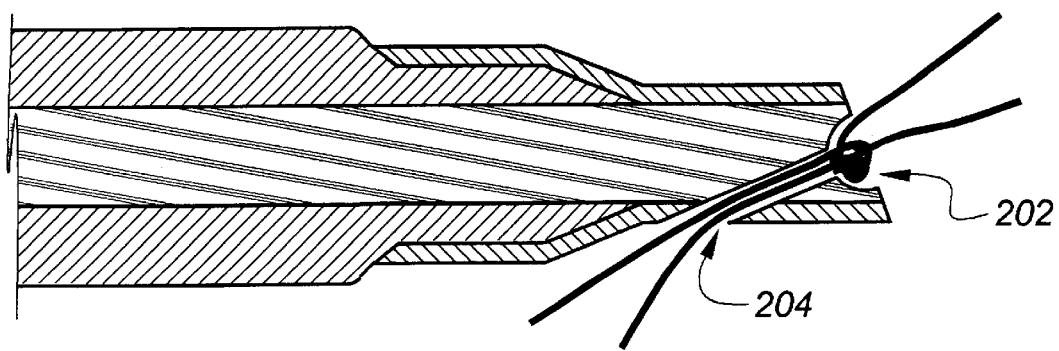
FIG. 2 is a close-up of a tip having a concave suture knot retaining feature for arthroscopic/laproscopic procedures, in particular.

FIG. 2 illustrates an alternative embodiment of the invention, wherein the knot-retaining feature is a cup-shaped recess 202. The heating element in this case preferably forms at least a portion of the surface of the recess, or may be located elsewhere but close enough to permit sufficient thermal transfer. The electrical configuration in this case is monopolar, such that the conduction path to the heating element is completed through the body of the patient and a suitable grounding pad. Such an arrangement permits the tip to fit into a standard Bovie handle. Bipolar operation may be provided through suitable modification.

In the embodiment of FIG. 2, a channel 204 is provided in physical communication with the recess 202, enabling suture material to be dressed therethrough. A tied knot, retained within the region 202, is heated and sealed, and the materials through the channel 204 severed. Although the channel 204 is shown in FIG. 2 as an enclosed tube, the channel 204 may take the form of an open groove or other configuration, enabling thread to be snapped in from the side of the tip rather than routing the material through a tube.

When used for arthroscopic/laproscopic procedures, instruments according to the invention may need to operate when surrounded by body fluid. In such cases, the fluid may cause heat generation to be less efficient, which, in turn, may require excess energy or time to complete the heat-sealing procedure. Accordingly, when an inventive device is used invasively, a gas is preferably trapped or generated around the knot to be sealed. This may be accomplished in different ways according to the invention, including the use of a temperature sufficient to naturally form a gas bubble in the region where the knot is being sealed. Alternatively, a conduit may be provided, preferably from the handle of the device, to actively delivery a small amount of gas to the knot-sealing site. A nonflammable gas such as oxygen or nitrogen may be used, and the instrument itself may be cannulated to provide the gas-carrying conduit.

We claim:

1. A device for sealing a suture knot, comprising:

an elongated instrument having a proximal end adapted for gripping by a user and a distal tip;

a cup-shaped suture knot retaining feature associated with the distal tip including a suture retaining channel in physical communication with the retaining feature;

a heating element located proximate to the suture knot retaining feature;

a source of electrical power; and a user control enabling the user to selectively apply the electrical power to the heating element so as to heat-seal a suture knot held within the suture knot retaining feature.

2. The device of claim 1, wherein the suture retaining channel is an open grove.

3. The device of claim 1, wherein the suture retaining channel is an enclosed tube.

4. The device of claim 3, wherein the suture knot retaining feature includes an aperture into the enclosed tube.

5. The device of claim 1, wherein the electrical connection from the source of electrical power is unipolar, using the body of a patient as a return path.

6. The device of claim 1, wherein the distal tip of the instrument is removable.

7. The device of claim 1, wherein the temperature to which the heating element is raised is sufficient to heat-seal the suture knot when surrounded by fluid within a body cavity.

8. The device of claim 1, wherein the temperature to which the heating element is raised is sufficient to form a gaseous bubble within the suture knot retaining feature.

9. The device of claim 1, further including a conduit carrying a gas to the suture knot retaining feature, so that the knot is heat-sealed within the gas as opposed to a fluid when the distal tip is positioned within a body cavity.

10. The device of claim 1, further including a suture cutter.

11. A method of sealing a suture knot, comprising the steps of:

providing an elongated instrument having a proximal end adapted for gripping by a user and a distal tip with a suture knot retaining feature that may be heated under user control;

positioning a suture knot within the suture knot retaining feature;

applying heat sufficient to seal the knot; and forming a gas around the knot prior to or during the application of heat to the knot.

12. The method of claim 11, wherein:

the suture knot retaining feature further includes a cup-shaped knot holder and a suture retaining channel in physical communication with the knot holder; and the method further includes the steps of:

positioning the suture material that comprises the knot into the channel; and sliding the knot onto a piece of the suture material prior to applying heat sufficient to seal the knot.

13. The method of claim 12, wherein the step of sliding the knot onto a piece of the suture material includes the step of using a Tennessee slider knot.

14. The method of claim 11, wherein the step of forming a gas around the knot includes the step of raising the temperature of the suture retaining feature to a point sufficient to form a gas bubble when the distal tip is surrounded by fluid.

15. The method of claim 11, wherein the step of forming a gas around the knot includes the step of actively delivering a gas to the suture retaining feature through a conduit provided for such purpose.

* * * * *